United States Patent [19]
Hammerslag et al.

[11] Patent Number: 5,378,234
[45] Date of Patent: Jan. 3, 1995

[54] COIL POLYMER COMPOSITE

[75] Inventors: Gary R. Hammerslag, Dana Point; John Merritt, San Clemente; Mark Nielsen, San Juan Capistrano, all of Calif.

[73] Assignee: Pilot Cardiovascular Systems, Inc., San Clemente, Calif.

[21] Appl. No.: 62,961

[22] Filed: May 14, 1993

Related U.S. Application Data

[63] Continuation-in-part of Ser. No. 31,810, Mar. 15, 1993.

[51] Int. Cl.⁶ .............................................. A61M 37/00
[52] U.S. Cl. ..................................... 604/95; 604/282; 138/129
[58] Field of Search .......... 604/95, 280, 282, 164–167; 128/4, 6; 138/129

[56] References Cited

U.S. PATENT DOCUMENTS

| | | |
|---|---|---|
| 33,166 | 2/1890 | Samson . |
| 3,470,876 | 10/1969 | Barchilon . |
| 3,521,620 | 7/1970 | Cook . |
| 3,547,103 | 12/1970 | Cook . |
| 3,605,725 | 9/1971 | Bentov . |
| 4,236,509 | 12/1980 | Takahashi et al. ................. 128/4 |
| 4,456,017 | 6/1984 | Miles . |
| 4,676,249 | 6/1987 | Arenas et al. . |
| 4,719,924 | 1/1988 | Crittenden et al. . |
| 4,723,936 | 2/1988 | Buchbinder et al. . |
| 4,753,223 | 6/1988 | Bremer . |
| 4,757,827 | 7/1988 | Buchbinder et al. . |
| 4,758,222 | 7/1988 | McCoy . |
| 4,815,478 | 3/1989 | Buchbinder et al. . |
| 4,850,351 | 7/1989 | Herman et al. . |
| 4,886,067 | 12/1989 | Palermo . |
| 4,898,577 | 2/1990 | Badger et al. . |
| 4,899,787 | 2/1990 | Ouchi et al. ........................... 128/4 |
| 4,940,062 | 7/1990 | Hampton et al. . |
| 5,024,654 | 6/1991 | Tyler . |
| 5,084,012 | 1/1992 | Kelman . |
| 5,108,368 | 4/1992 | Hammerslag et al. . |
| 5,176,126 | 1/1993 | Chikama . |
| 5,195,968 | 3/1993 | Lundquist et al. . |

FOREIGN PATENT DOCUMENTS

343509  11/1989  European Pat. Off. .

*Primary Examiner*—John D. Yasko
*Attorney, Agent, or Firm*—Darby & Darby

[57] ABSTRACT

A coil polymer composite tubular body is disclosed, such as for use in medical applications. The body comprises a spring coil having at least one central lumen extending axially therethrough, for receiving medical implements, fiber optics, suction or transmission of fluids such as for irrigation or drug delivery. An elastomeric layer on the spring coil provides a substantially water impermeable seal. In one particular embodiment, the composite tubular body is provided with a laterally deflectable distal tip.

17 Claims, 3 Drawing Sheets

COIL POLYMER COMPOSITE

BACKGROUND OF THE INVENTION

This is a continuation-in-part of U.S. patent application Ser. No. 08/031,810 filed Mar. 15, 1993 which is currently pending.

The present invention relates to coil polymer composites. More particularly, the present invention relates to flexible coil polymer composites for use in medical guidewires, catheters, and, other medical devices.

Medical catheters generally comprise elongate tube-like members which may be inserted into the body, either percutaneously or via a body orifice, for any of a wide variety of diagnostic and therapeutic purposes. Such medical applications generally require the use of a catheter having the ability to turn corners, such as in ocular irrigation and aspiration applications, or to negotiate twists and turns, such as in certain cardiovascular applications.

For example, percutaneous transluminal coronary angioplasty (balloon angioplasty), requires manipulation of a catheter from a proximal position outside the patient's body through branched and tortuous portions of the patient's arterial system for the purpose of alleviating an obstruction by inflating a balloon. This particular procedure has been performed with increasing frequency over the past years in preference to open heart bypass surgery, when possible.

In another application, transluminal laser catheter angioplasty (laser angioplasty), the delivery of laser energy from an external source to an intraluminal site to remove plaque or thrombus obstructions in vessels is accomplished by providing a waveguide such as a fiber optic bundle within a catheter. The nature of laser angioplasty requires an even greater ability to precisely manipulate the catheter, to control and aim the laser light at the specific plaques or thrombi to be removed.

A variety of other medical applications require or would benefit from the use of a coil polymer composite housing, together with the steering mechanism disclosed herein, which may be coupled with or incorporated into an endoscope or other multi-functional catheter. For example, one ocular application involves removal of a diseased lens, and replacement with any of a variety of prosthetic intraocular lenses. The native lens is encased in a capsular bag, including a front portion closest to the cornea known as the anterior capsule and a rear portion known as the posterior capsule.

An irrigation and aspiration instrument is advanced through an incision in the cornea and through the anterior wall of the capsular bag. Due to the geometry involved, the distal tip of the irrigation and aspiration tool cannot conveniently reach various regions within the capsular bag. The irrigation and aspiration tool must be both flexible, and capable of transmitting either vacuum or fluid under pressure.

For each of the foregoing applications, there remains a need for a small diameter tubular housing structure, which may be readily adapted for use in the construction of steerable guidewires, catheters and other implements. For many applications, the catheter preferably has optimum flexibility and pushability, yet minimal outer diameter and wall thickness. In addition, the tubular wall is preferably fluid tight, to permit transmission of fluids or gas therethrough either under pressure or vacuum.

SUMMARY OF THE INVENTION

There is provided in accordance with one aspect of the present invention a coil polymer composite tubular body of the type for use in the construction of medical devices. The composite tubular body comprises an elongate tubular spring coil support, and an elastomeric coil extending along and interfit within at least a portion of the spring coil support.

The spring coil support and the elastomeric coil cooperate to provide a flexible composite tubular body having at least one central lumen extending therethrough, and a substantially water impermeable wall. Preferably, the polymer comprises silicone.

In one embodiment, adjacent loops of the coil are spaced axially apart along at least a portion of the length of the coil. The elastomeric coil substantially fills the space between adjacent coil loops.

In accordance with another aspect of the present invention, there is provided a steerable sheath, such as for incorporation into any of a variety of medical implements. The steerable sheath comprises an elongate flexible tubular housing, having proximal and distal ends and at least one central passageway extending axially therethrough.

A deflection element is secured to the housing at a first point, and extends axially along the housing. A pull element is secured to the housing at a second point, and extends axially along the housing. The second point is preferably rotationally displaced from the first point.

A spring coil is provided in the wall of at least a portion of the housing, and an elastomeric layer is provided for surrounding the spring coil.

Axial proximal displacement of the pull element causes a lateral displacement of a portion of the tubular housing.

In accordance with a further aspect of the present invention, there is provided an irrigation and aspiration tool incorporating the coil polymer composite and steering mechanisms of the present invention. The irrigation and aspiration tool comprises a tubular spring coil body, having a flexible distal region thereon. An elastomeric layer is provided, extending along the spring coil body. A pull wire extends proximally from a distal end of the tubular body. Proximal axial displacement of the pull wire causes a lateral deflection of the flexible end of the tubular body.

Preferably, an axially reciprocally movable tubular sleeve is provided, spaced radially outwardly apart from the spring coil to provide an annular flow passage therethrough.

Further features and advantages of the present invention will become apparent from the detailed description of preferred embodiments which follows, when considered together with the attached claims and drawings.

DETAILED DESCRIPTION OF PREFERRED EMBODIMENTS

There is provided in accordance with one aspect of the present invention an embodiment of a steerable medical device in the form of a steerable tubular sheath, for gaining access to and/or pointing within the body. Any of a wide variety of working implements, such as fiber optics, irrigation, aspiration, balloon dilatation catheters, biopsy or other tissue removal apparatus, and the like can readily be adapted for use through the central lumen of the steerable sheath. Preferably, the steerable sheath is provided with a coil polymer composite tubular body, as discussed infra in connection with FIGS. 6–8.

Figure 1:
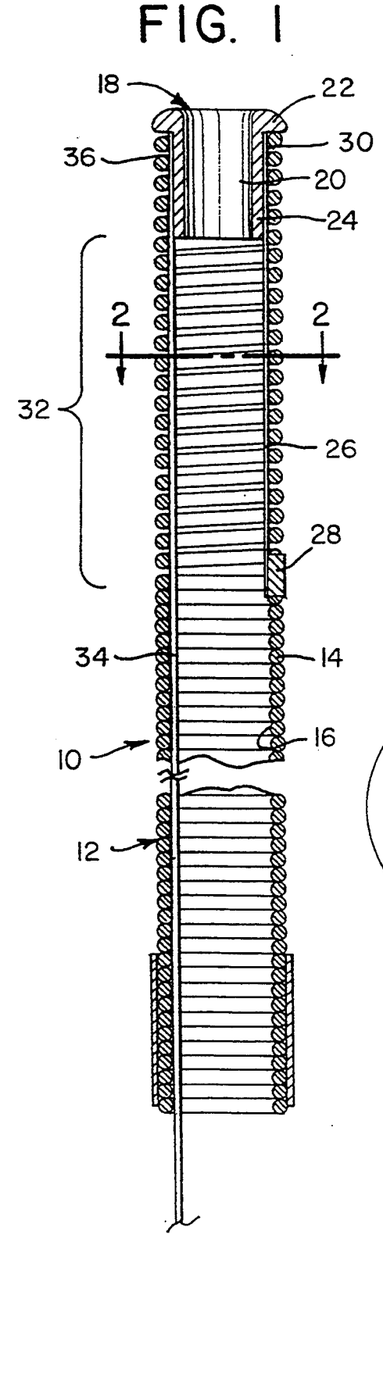
FIG. 1 is a cross-sectional elevational view of the distal end of a steerable tubular sheath in accordance with one aspect of the present invention.

Referring to FIG. 1, there is provided a steerable sheath 10 in accordance with the present invention. Steerable sheaths and/or coil polymer composite housings in accordance with the present invention, coupled with or incorporated into an endoscope or other multifunctional catheter, can be used in any of a wide variety of medical and nonmedical applications. Medical applications of particular interest include gastroenterology, urology, gynecology, ear, nose and throat applications, orthopedics (arteroscopy), angioscopes, neurology and cardiology.

Figures 2, 3:
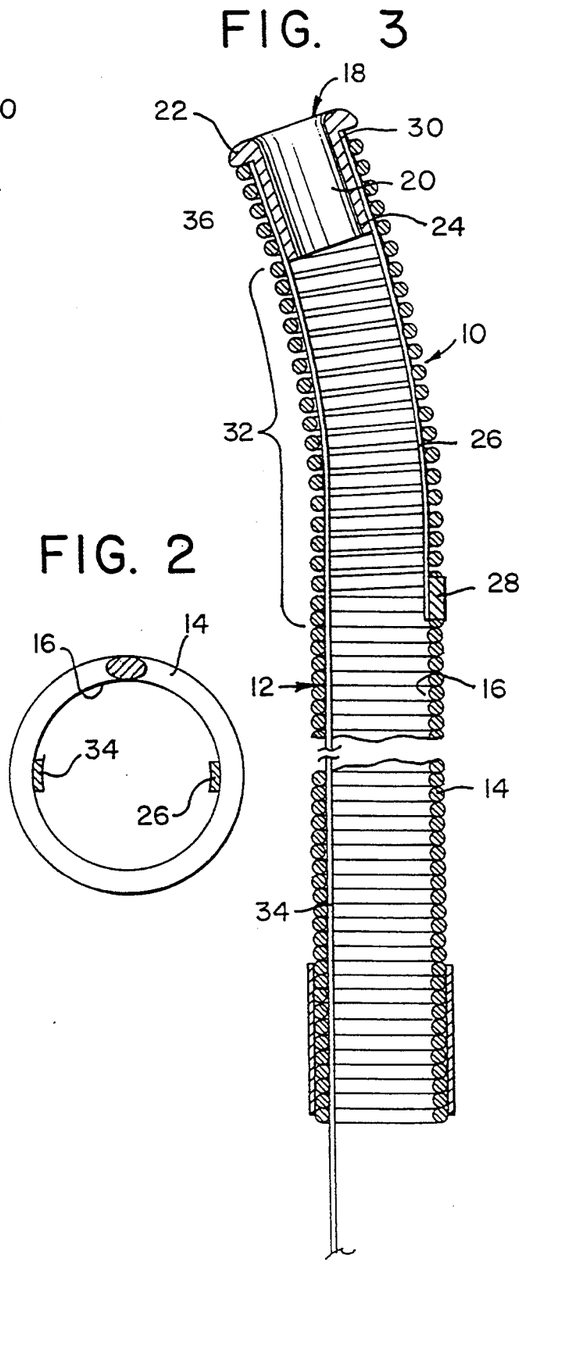
FIG. 2 is a cross-sectional view through lines 2—2 of FIG. 1.
FIG. 3 is a cross-sectional elevational view of the steerable sheath of FIG. 1, shown in a deflected configuration.

In general, the steerable sheath of the present invention is applicable in any environment in which it is desirable to controllably deflect the distal tip of a working implement. Alternatively, the coil polymer composite body can be readily incorporated into nonsteerable devices, as will be apparent to one of skill in the art. The steerable sheath embodiment illustrated in FIGS. 1-3 can be readily adapted to a desired application by one of skill in the art. The embodiment illustrated in FIGS. 4 and 5 has been particularly adapted for use as an ocular irrigation and aspiration tool, as will be discussed infra.

Steerable sheath 10 generally comprises an elongate tubular body 12 which is laterally flexible at least in the distal steering region 32 thereof. For certain applications, such as ocular surgical procedures, only the distal steering region 32 of the sheath 10 is preferably flexible. For other applications such as endoscopes and cardiovascular catheters, the sheath is preferably flexible as far proximally of steering region 32 as is desirable for the intended application.

Tubular body 12 generally comprises a spring coil portion 14, as is well known in the art. Spring coil 14 may additionally be coupled to a proximal hypodermic needle tubing section, as is known in the art. Spring coil 14 defines a central elongate lumen 16 for guiding surgical implements, fluids or vacuum axially through the sheath 10 and out a distal opening 18. Depending upon the intended application, the central lumen 16 can be readily divided into two or more passageways such as for carrying fiber optic illumination and visualization bundles, irrigation, aspiration, drug delivery, balloon inflation or other conduits as well as wiring for transducers and working channels for any of a wide variety of known medical implements.

In an embodiment of the steerable sheath useful in spinal endoscopy, the section of spring coil 14 extends approximately 16 inches or more in length. Adjacent windings of the spring coil 14 ("filars") are typically "bottomed out" as is known in the art, with adjacent filars in the distal most one quarter to one half inch being spaced apart by about a 0.005–0.006 inch gap. The outside diameter of the steerable endoscope sheath is approximately 0.100 inches. In this embodiment, the spring coil extends the entire length of the sheath, and no proximal hypotube section is generally provided.

In a preferred embodiment, an end cap 20 or other lateral force transmitting structure is provided at the distal opening 18. End cap 20 in the illustrated embodiment comprises a radially extending annular flange 22 with a smooth outer surface for minimizing trauma as the tubular sheath 10 is advanced distally through the body. End cap 20 is preferably additionally provided with one or more axially extending support structures such as annular flange 24 which extends in a proximal direction through central lumen 16 to securely anchor cap 20. Axial flange 24 and radial flange 22 provide convenient mounting surfaces for attachment of the deflection ribbon 26 and pull ribbon 34, discussed infra.

End cap 20 may comprise any of a variety of configurations and materials, as will be apparent to one of skill in the art. Preferably, end cap 20 comprises a material which is readily securable to the deflection ribbon 26 and pull ribbon 34 such as by brazing or soldering techniques. Typically, end cap is also secured to the spring coil 14.

Alternative structures to replace end cap 20 can be devised as needed for particular applications or manufacturing convenience. For example, axial flange 24 can be replaced by one or more support structures which extend less than the full circumference of spring coil 14. Alternatively, the function of end cap 20 can be accomplished by fusing the distal most filars of spring coil 14 together such as by flowing solder therebetween in a manner that maintains patency of lumen 16. In general, any structure that laterally transfers force between deflection ribbon 26 and pull ribbon 34, and which preferably also resists axial collapse of the spring coil, is preferred.

The portion of spring coil 14 which extends around axial flange 24 is relatively inflexible. Thus, the axial length of axial flange 24 can be varied to affect the deflected profile of the steerable sheath 10. Preferably, the axial flange 24 is less than about 0.5 inch long, and, more preferably, axial flange 24 is less than about 0.2 inch long. Too short an axial flange 24 may adversely impact the integrity of the joint between end cap 20 and spring coil 14, and an annular flange 24 of at least about 0.100 inches long is preferred in a steerable sheath having a diameter of about 0.100 inches.

A deflection ribbon 26 is preferably secured with respect to the tubular body 12 at a proximal point 28, and extends distally to a distal point of attachment 30. The distal point of attachment may secure the deflection ribbon 26 to either or both of the spring coil 14 and end cap 20. Deflection ribbon 26 bends upon axial displacement of pull ribbon 34, with proximal point of attachment 28 functioning as a fulcrum or platform.

Proximal attachment 28 is preferably a solder, braze or weld joint, as is known in the art, with any excess on the radial outside surface of the tubular body 12 being trimmed or polished to minimize rough edges. Distal point of attachment 30 is similarly provided by any of a variety of conventional securing techniques which is appropriate for the construction materials of the steerable sheath 10.

The length of the space between the proximal point of attachment 28 and distal point of attachment 30 affects the radius of the curve of the deflection ribbon 26 and hence of the region 32, as will be appreciated by one of skill in the art. The deflection ribbon 26 in the preferred embodiment will tend to remain positioned along the exterior circumference of the curve during deflection of the steerable sheath 10. Since the circumference in a given steerable sheath 10 will be a fixed distance, the radius of the curve during deflection will differ, depending upon the degree of deflection achieved.

For example, in a steerable sheath 10 as illustrated in FIG. 1 having an exterior diameter of about 0.100 inches and a distance of 0.315 inches between the first and second points of attachment, a 45° bend in the steerable sheath 10 will produce a 7.5 mm inside curve radius (10 mm outside radius). In order to achieve a 7.5 mm inside curve radius for a bend of 90°, the distance between points of attachment 28 and 30 must be extended to 0.630 inches.

Deflection at steering region 32 of steerable sheath 10 is accomplished by providing a pull ribbon 34. Pull ribbon 34 is preferably secured at a distal point of attachment 36 and extends proximally to the control end of the steerable sheath 10. Axial displacement of the pull ribbon 34 will tend to pivot the steering region 32 of the tubular body 12 around proximal point of attachment 28. Preferably, lateral displacement of steering region 32 is accomplished by axial proximal displacement of pull ribbon 34.

Two or more pull ribbons 34 can be provided in accordance with the same basic principles. See, e.g., U.S. Pat. No. 5,108,368 to Hammerslag, et al., the disclosure of which is incorporated herein by reference. However, in a simplified, single plane steerable sheath 10, a single pull ribbon 34 is sufficient.

Pull ribbon 34 is rotationally offset from deflection ribbon 26 by at least about 90°. Preferably, pull ribbon 34 is rotationally offset from deflection ribbon 26 by about 180°, as illustrated in FIG. 1 and cross-sectional view FIG. 2. Among other advantages of this configuration, opposing placement of deflection ribbon 26 and pull ribbon 35 tends to maintain central lumen 16 open while the steering region 32 is laterally deflected in response to proximal displacement of pull ribbon 34. This tends to prevent objects traveling through central lumen 16 from becoming entangled with pull ribbon 34 or deflection ribbon 26.

In another embodiment, an interior tubular sleeve (not illustrated) is additionally provided to facilitate negotiation of objects or fluids through central lumen 16. The interior sleeve is preferably in the form of a continuous, tubular flexible material, such as nylon or polyethylene. In an embodiment of the tubular sheath in which the catheter has an outside diameter of 0.100 inches (0.098 inch coil with a 0.001 inch thick outer sleeve) and an inside diameter of 0.078 inches, the interior tubular sleeve may have an exterior diameter in the area of about 0.074 inches and an interior diameter in the area of about 0.069 inches. The use of this thin wall plastic tube on the inside of the tubular sheath 10 is particularly useful for guiding a fiber through the tubular sheath 10. The interior tube described above is additionally waterproof, and can be used to either protect the implements transmitted therethrough from moisture, or can be used to transmit fluids through the steerable sheath 10.

In one embodiment of the steerable sheath illustrated in FIG. 1, the spring coil 14 is wound from a filar stock having a 0.010-inch diameter. The spring coil is tightly wound or "bottomed out" from its proximal end through the proximal point of attachment 28. From the proximal point of attachment 28 to the distal point of attachment 30, the adjacent loops of the spring coil are preferably spaced slightly apart (e.g., 0.005–0.006 inches) to facilitate flexibility and bending, as is well known in the art. However, it has been determined that in an embodiment utilizing an end cap 20, as illustrated, wherein the end cap is secured to deflection ribbon 26 and pull ribbon 34 but not to the spring coil 14, spring coil 14 can be bottomed out within the distance between proximal point of attachment 28 and distal point of attachment 30.

In a preferred embodiment for carrying and aiming a fiber optic through the cardiovascular system, 0.010-inch wire stock is wound into a coil having an outside diameter of about 0.098 inches and an inside diameter of from about 0.078 to about 0.080 inches. The pull ribbon 34 comprises a flat ribbon of high-tensile strength stainless steel having a cross-sectional dimension of about 0.003 by about 0.010 inches. The deflection ribbon 26 preferably comprises a material such as spring-tempered stainless steel or Elgiloy ®, available from Elgiloy Ltd. Partnership, Elgin, Ill. Elgiloy ® may be desirable in embodiments required to permit relatively higher degrees of curvature, as it does not take a set as easily as the stainless steel deflection ribbon 26. In general, materials such as Elgiloy ® which will not exceed their elastic limit as easily as stainless steel are preferable in embodiments which are required to undergo particularly extreme curvature in use.

Preferably, an outer tubular sleeve is provided for surrounding the tubular body 12 at least throughout the length of spring coil 14. The outer tubular sleeve may be provided in accordance with techniques known in the art and, in one embodiment, is a thin wall polyester heat shrink tubing such as that available from Advanced Polymers, Inc. in Salem, N.H. Such heat shrink tubings have a wall thickness of as little as about 0.0002 inches and tube diameter as little as about 0.010 inches. The outer tubular sleeve enhances the structural integrity of the sheath, and also provides a fluid seal and improved lubricity.

For example, the outer tubular sleeve tends to prevent the spring coil from collapsing under proximal force on pull wire 34. In general, in an embodiment of the steerable sheath 10 for use with a 0.055 inch diameter central fiber bundle, a pulling force on pull wire 34 in the area of from about 2½ pounds to about 5 pounds may be necessary to bend the fiber optic. If the outer tubular sleeve is deleted, adjacent windings of spring coil 16 may become misaligned under these forces. The sleeve also improves pushability of the catheters, and improves torque transmission.

Figures 4, 5, 6:
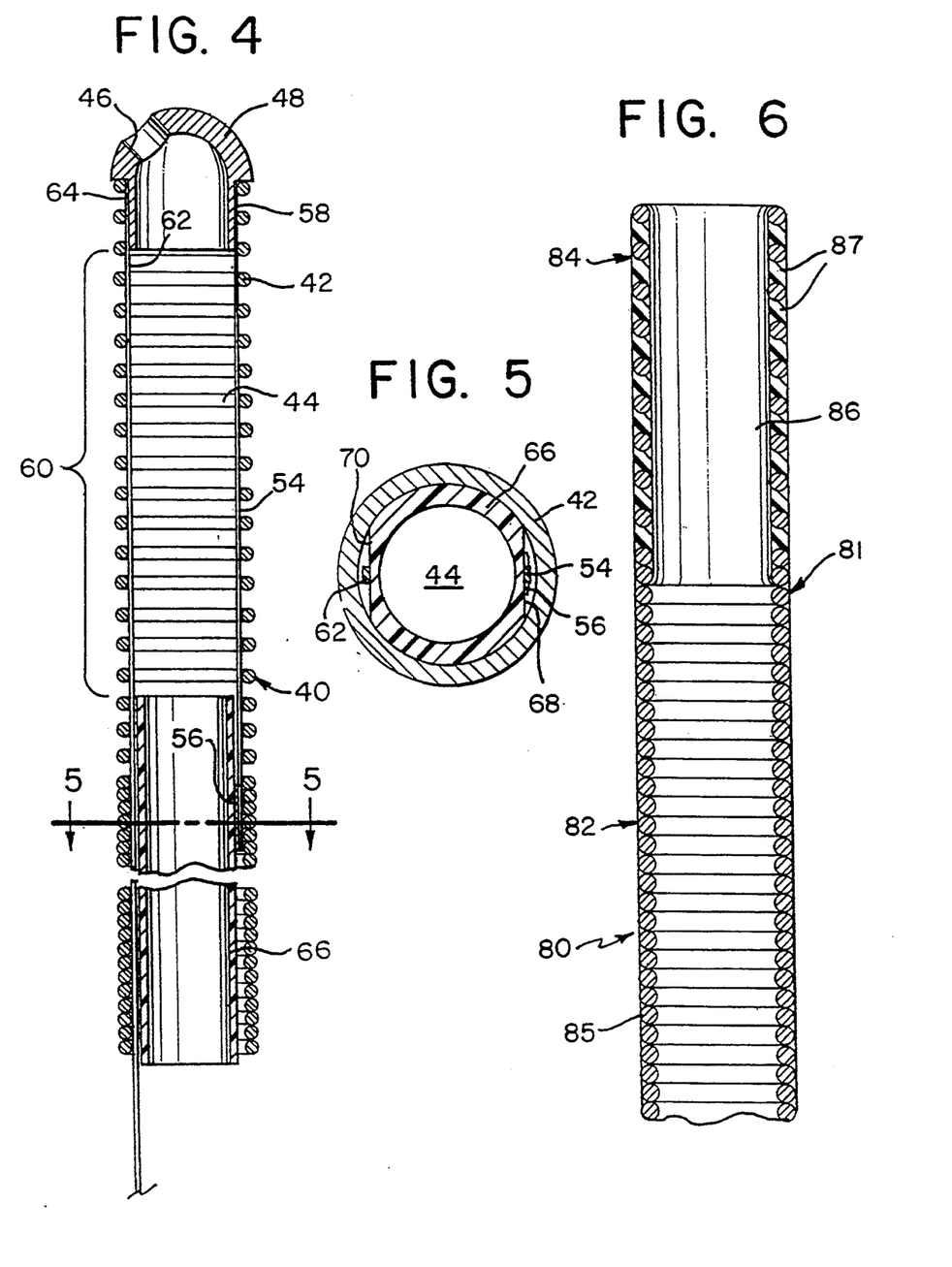
FIG. 4 is a cross-sectional elevational view of the distal end of a steerable aspiration device, in accordance with a further aspect of the present invention.
FIG. 5 is a cross-sectional view along linen 5—5 in FIG. 4.
FIG. 6 is a cross-sectional elevational view of a tubular spring coil body incorporating the coil polymer composite of the present invention.

Referring to FIGS. 4 and 5, there is illustrated a modified embodiment of the steerable tubular sheath of the present invention, particularly adapted for irrigation and aspiration of interior regions of the human eye. However, any of the features of the embodiment of FIGS. 4 and 5 can readily be adaptable or combinable into the previous embodiments disclosed herein, such as for application within the cardiovascular, gastrointestinal or other body lumens, tissue or organs, as desired.

A variety of medical conditions can give rise to a cataract or opaque lens. One method of treating the opaque lens is by removal, and replacement with any of a variety of prosthetic intraocular lenses.

A variety of instrumentation has been developed for removal of the lens material. For example, U.S. Pat. No. 5,084,012 to Kelman discloses both rigid linear and flexible precurved irrigation and aspiration catheters for this purpose. In general, the elongated catheter tip is inserted through an incision made in the cornea. The instrument is said to be capable of vibrating the operative tip at ultrasonic frequencies of variable amplitude and duration to break apart particles of the material, such as a cataracted lens. Sources of fluid and vacuum are provided at the proximal end of the instrument to dispense and withdraw fluid to and from the surgical site.

The opaque lens or cataract to be removed is encased in a membrane or capsular bag, including a front portion closest to the cornea, known as the anterior capsule and a rear portion known as the posterior capsule.

The removal instrument is advanced through the incision in the cornea and also through an incision in the anterior wall of the capsular bag. Due to the geometry involved, as is well understood in the art, the distal tip of the irrigation and aspiration tool can not conveniently reach various regions within the capsular bag, particularly around the peripheral portions at the junction of the anterior and posterior walls. The ability of the irrigation and aspiration tool disclosed herein to controllably bend in as far as a 180° or greater curve permits significantly improved access to all regions within the capsular bag, as will be apparent to one of skill in the art in view of the disclosure herein.

Referring to FIG. 4, the modified steerable sheath comprises an elongate tubular body 40 having a spring coil section 42 disposed on the distal end thereof. Spring coil section 42 may in an ocular application be considerably shorter than in a cardiovascular application, as will be understood by one of skill in the art.

Spring coil 42 defines a central lumen 44 for placing a distal opening 46 in fluid communication with a proximal vacuum or source of infusion media. The spring coil wall is rendered fluid tight such as by an outer shrink tubing (not illustrated) as has been discussed. Multiple infusion or vacuum lumen can readily be provided, as desired, such as for simultaneous irrigation and aspiration or other functions known in the art.

In one embodiment of the steerable sheath intended for ocular applications, an outer tubular irrigation sleeve is provided, spaced apart from and surrounding the spring coil 42. The outer tubular sleeve in one embodiment has an inside diameter of about 0.060 inches and an outside diameter of about 0.075 inches for use on a steerable sheath having an outside diameter of spring coil 42 of about 0.040 inches. This configuration provides an annular flow passageway in the annular space between the spring coil 42 and the outer sheath (not illustrated). The distal end of the outer irrigation sleeve is positioned sufficiently close to the distal end of the device so that it will be positioned within the capsule of the eye when in use. In one preferred embodiment, the outer distal sleeve is positioned no more than about 2 mm from the distal tip of the catheter.

Preferably, the outer irrigation sleeve is axially reciprocally movable with respect to spring coil 42. In addition, the irrigation sleeve is preferably secured at its proximal end with respect to pull wire 62. In this manner, axial proximal displacement of the irrigation sleeve simultaneously causes lateral deflection of the steering region 60. This configuration provides a preferred result of causing the spring coil 42 to simultaneously curve as it is advanced out of the distal end of the outer sleeve.

Distal opening 46 may be conveniently provided in an end cap 48 which is otherwise constructed in a manner similar to end cap 20 of the previous embodiment. Preferably, distal opening 46 is inclined with respect to the longitudinal axis of tubular body 40. Preferably, an angle of about 45° is provided, although other angles can be used as will be understood by one of skill in the art.

In a steerable sheath adapted for the ocular irrigation and aspiration (IA) application, the steering region 60 extends approximately from the distal end of hypotubing 66 to the distal point of attachment 58 with respect to cap 48. The steering region 60 in an IA device will typically be less than about 0.25 inches in length, and preferably less than about 0.200 inches.

In one particular embodiment, the distance between distal point of attachment 58 and distal end of hypotube 66 is approximately 0.175 inches. In that embodiment, the distance from distal point of attachment 58 to the distal tip of end cap 48 is approximately 0.040 inches. The outside diameter of the spring coil 42 is approximately 0.040 inches, and the inside diameter of spring coil 42 is approximately 0.033 inches. The inside diameter of hypotube 66 is approximately 0.026 inches. Preferably, the outside diameter of the tubular body 40 is substantially uniform throughout its length; however, only the distal most 0.5 inches is likely to be introduced within the eye. Portions of the tubular body 14 which are spaced more than about 0.75 inches from the distal end of end cap 48 therefore need not maintain the same exterior diameter.

Deflection of steering region 60 is accomplished in a manner similar to that previously described, with one or more deflection ribbons 54 extending from a proximal point of attachment 56 to a distal point of attachment 58. Preferably, adjacent windings of the spring coil 42 throughout the steering region 60 are slightly spaced apart as has been previously described. The proximal point of attachment 56 may coincide with the distal end of hypotube 66, and, preferably, comprises a solder joint or other secure junction which joins the spring coil 42, proximal end of deflection ribbon 54, and the distal end of hypotube 66.

Deflection is further accomplished through the use of a pull ribbon 62, which is secured at a distal point of attachment 64 to end cap 48 or other lateral force transmitting structure.

In one embodiment of the invention, the proximal end of pull wire 62 is soldered or otherwise secured with respect to the spring coil 42 at a point proximally of the distal end of hypotube 66. In this manner, steering may be accomplished by grasping the proximal extension of hypotube 66 and axially sliding spring coil 42 in a proximal or distal direction with respect to hypotube 66. The proximal end of spring coil 42 may be secured to any of a variety of friction enhancing structures or handles to facilitate axial manipulation of spring coil 42 with respect to hypotube 66.

The concentric arrangement of the spring coil 42 with respect to hypotube 66 is further illustrated in FIG. 5. At the illustrated cross section, hypotube 66 is axially slidably received within spring coil 42. An axially extending deflection ribbon flat 68 is milled, ground or otherwise provided along an exterior surface of hypotube 66, for receiving deflection ribbon 54. Deflection ribbon 54 is preferably secured to the hypotube at a proximal point of attachment 56 such as by soldering, or other attachment means which does not interfere with axial slidability of the hypotube 66 within spring coil 42.

Similarly, an axially extending pull ribbon flat 70 is provided on the opposing side of hypotube 66, for slidably receiving pull ribbon 62. In an embodiment where pull ribbon 62 extends through a channel provided by pull ribbon flat 70, straightening of a displaced steering region 60 can be achieved by distal axial displacement of pull ribbon 62 as will be understood by one of skill in the art.

In one preferred embodiment of the IA tool, the steering region 60 between proximal point of attachment 56 and distal point of attachment 58 is approximately 0.175 inches, which permits a 180° deflection of the steering region 60 with respect to the longitudinal axis of tubular body 40, around an inside curve radius of about 0.015 inch. Deflections of as much as 180° or more are preferably obtainable for use in IA procedures, in order to insure access to the entire interior of the lens capsule as will be understood by one of skill in the art.

The IA tool tip is further provided with an interior and/or exterior tubular sleeve for efficiently transmitting vacuum or pressurized fluids from the proximal end of the tubular body 40 to the distal port 46. In one preferred embodiment, an outer tubular sleeve is securely adhered around the outside of spring coil 42, to provide an efficient seal. One preferred outer tubular sleeve is a thin wall low density polyethylene tubing such as that available from Medical Extrusion Technologies in Murietta, Ca. Alternatively, a polyester heat shrink tubular sleeve such as that available from Advanced Polymers, Inc., as has been previously discussed, can also be used. Alternatively, other techniques for waterproofing a spring coil can be devised.

Referring to FIG. 6, there is disclosed a coil polymer composite subassembly 80 in accordance with a preferred embodiment of the present invention. The illustrated coil polymer composite subassembly 80 comprises a tubular spring coil body 81 having a bottomed out region 82 in which adjacent coil filars are in contact with one another, and a stretched section 84 in which adjacent coil filars are spaced apart from one another. Although the utility of the present invention is maximized in a section of spring coil such as 84 where adjacent filars are spaced apart for optimum flexibility, the invention is also advantageous in bottomed out spring coil segments such as 82.

A polymer coil 86 fills the spaces between adjacent coil filars in the stretched region 84, to produce a fluid-tight tubular body. Preferably, the polymer additionally fills interstitial spaces 85 between adjacent coil filars in the bottomed out region 82, on the radial exterior and/or radial interior surfaces of the coil, to produce a sealed tubular composite body 80.

Adjacent segments of polymer coil 86 are preferably connected across the intervening filar by a connective layer 87 as described infra. Thus, the polymer component of the composite may take the form of a tubular sleeve having a radially inwardly extending spiraling flange or thread. The depth of the thread in the radial direction depends upon whether the corresponding spring coil filars are bottomed out or spaced apart at a given location.

Alternatively, depending upon the method of applying the polymer, an additional connective layer may extend along the radially interior surface of the spring coil. The polymer component in this embodiment will be in the form of a cylindrical wall having a central lumen therethrough and a wall thickness at least slightly larger than the spring coil filar diameter.

The polymer is preferably sufficiently elastic to withstand the stretching and compressive forces experienced during flexing of the subassembly 80 without compromising the seal. In addition, in a medical application, the polymer is preferably substantially biologically inert and sterilizable. Silicone has been found to be particularly well suited for this purpose, although other materials may be selected through routine experimentation.

The application of silicone or other suitable polymer in accordance with this aspect of the present invention produces a different structure than conventional heat shrinking of tubing around the periphery of a coil, although heat shrink tubing may in the future be developed which can accomplish the objectives of the present invention. In accordance with the present invention, a helical coil 86 of polymer is provided to continuously join adjacent spring coil filars into a composite tubular body. The polymer coil 86 is disposed substantially entirely between adjacent filars, generally with a relatively minor outer connective layer 87 extending across the radially outward most surface of the filar. The thickness of the outer connective layer 87 can be increased in an embodiment where the maximum desired exterior diameter permits.

Thus, polymer contacts substantially all and preferably all of the surface of the spring coil filar which is exposed in a direction parallel to the longitudinal axis of the tubular body. See FIG. 6. In between adjacent coil filars, the axially extending surfaces of the polymer coil 86 may be substantially parallel at rest as illustrated in FIG. 6. Alternatively, shrinkage or other factors may produce a thickness through the midpoint of one or more segments of polymer coil 86 which is slightly less than the filar diameter. This would produce a slightly concave outward meniscus like curve in the polymer segments between each filar. The thickness of the polymer coil in a radial direction can be varied to optimize desired physical properties of the finished device, such as torque transmission, pushability, flexibility, memory and burst strength or vacuum capacity.

In general, spring coil based medical devices for certain applications are advantageous over other designs for a variety of reasons. For example, coils are generally very flexible in a lateral direction which allows them to go easily around tight bends, yet they still transmit force very well in an axial direction which makes them very "pushable." Coils can be curved in a tight radius without kinking or changing the dimension of the inner lumen because the coil filars can separate along the outside radius of the curve. In addition, the stiffness of a coil can be varied in a variety of ways to produce discrete flexibility sections such as by stretching the coil to create a space between adjacent filars.

On the other hand, one difficulty with coil guidewire and catheter bodies compared to a polymeric or metal tube is that the inner lumen is not hermetic. This is particularly true in the distal region 84 where adjacent coil filars are spaced axially apart. Many applications of a steerable sheath or guidewire require hermeticity of the inner lumen for irrigation or aspiration purposes. The coil polymer composite of the present invention is directed to achieve both the benefits of the spring coil tubular body, as well as the hermeticity of the solid walled polymeric or hypodermic tube body designs.

Referring to FIG. 6, the polymeric coil 86 and connection layer 87 extends over and between adjacent filars. When the coil is coated in this way with the appropriate polymer, it becomes hermetic but the other advantageous properties of the spring coil remain substantially unchanged. The polymeric coating can be any of a variety of medical grade polymeric materials, which exhibit sufficient adhesion to produce a seal between adjacent filars and which retains its integrity even following significant and repeated bending of the catheter. Such materials are generally convertible from a first, relatively fluid state to a second, cured state by the application of an outside influence such as heat, catalyst or light.

Silicone has been found to be advantageous for this application because of its relative nonreactivity in the biological environment, and its extreme elastomeric properties. Even a relatively thin layer of silicone can be stretched significantly without ripping, and still return to its original shape. It can also sustain a significant amount of compression and return to its original shape. In addition, silicone is sufficiently flowable in its pre-cured state to provide a smooth outer and inner surface to the coil polymer composite. This advantageously minimizes trauma to tissue, and provides a smooth interior wall for the passage of implements or matter such as aspirated biological material.

One embodiment of the present invention was prepared using a two-part silicone dispersion system made by McGhan Nusil Corporation, Carpenteria, Ca., part No. MED2-4210. The silicone dispersion was thinned with 1,1,1-trichloroethylene to achieve a viscosity suitable for applying to the coil body.

The coil can be coated in any of a variety of ways. In the illustrated example, the silicone dispersion was painted onto the coil with a small piece of wire. The painted coil was thereafter positioned vertically and cured in an oven at about 300° F. for about 20 minutes. The coil can alternatively be coated such as by spraying or dipping into the silicone dispersion solution.

The silicone dispersion can be formulated in any of a variety of ways, as will be well known to one of skill in the art. For example, the dispersion can be formulated so that it will cure at room temperature, if desired. However, the working time in this formulation is greatly reduced. In addition, the surface tension and the viscosity of the silicone dispersion is preferably adjusted such as through the addition of 1,1,1,-trichloroethylene or other solvents to permit the dispersion to flow in between adjacent filars in the spaced region 84, yet not run down the inside or outside of the coil.

Alternatively, a one-part silicone adhesive can be used which cures when exposed to ambient air at room temperature, or at elevated temperatures such as in an oven. A one-part medical grade silicone adhesive for this purpose can be obtained from Dow Corning.

The resulting coil polymer composite subassembly 80 can be incorporated into any of a wide variety of medical or nonmedical tubular devices, as will be apparent to one of skill in the art. The composite subassembly 80 can include a tightly packed region 82 throughout, or a spaced apart region 84 throughout, as desired, depending upon the intended application of the structure.

Figure 7:
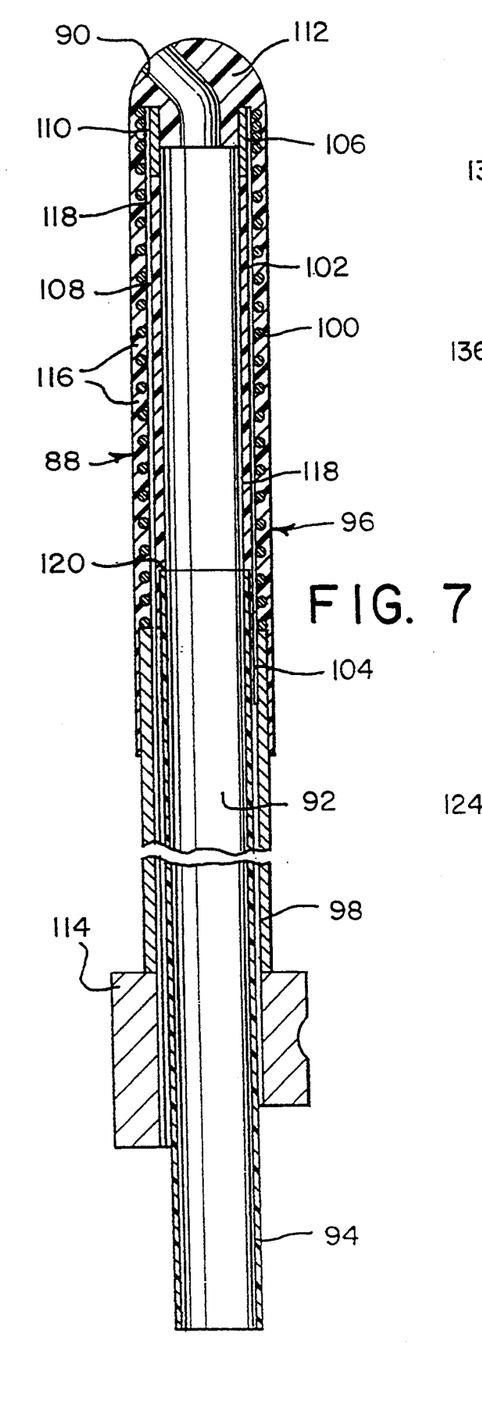
FIG. 7 is a cross-sectional elevational view of a coil polymer composite irrigation and aspiration device.

Referring to FIG. 7, there is disclosed an IA tool incorporating both a steering device and the coil polymer composite of the present invention.

The IA tool 88 is provided with a distal opening 90 in fluid communication by way of central lumen 92 with a proximal source of vacuum or infusate. The tubular body of IA device 88 comprises a proximal hypotube section 94 and a distal spring coil section 96. The spring coil section 96 generally comprises a proximal portion 98 having tightly packed adjacent coil filars, and a distal portion 100 having adjacent coil filars spaced axially apart.

A deflection ribbon 102 extends from a proximal point of attachment 104 to a distal point of attachment 106 as has been previously discussed. In addition, a pull ribbon 108 extends proximally from a distal point of attachment 110 at end cap 112. The proximal end of pull ribbon 108 is preferably secured to an axially reciprocally moveable annular pull sleeve 114. Axial displacement of pull sleeve 114 will cause a lateral deflection of the distal portion of the IA tool 88 as has been previously discussed.

Following assembly of the mechanical structures identified above, a curable polymer is applied to produce a coil polymer composite IA tool. Preferably, an elongate mandril having a diameter approximately equal to the inside diameter of hypotube section 94 is provided. The mandril is preferably coated with a release agent such as polyvinylpyrrolidone (PVP) or other coating which will prevent adhesion between the polymer and the mandril surface. Preferably, the pull wire 108 is also coated with PVP prior to installation. PVP is a water-soluble polymer obtainable, for example, from VWR Scientific, Inc., Cerritos, Ca., which may be mixed with ethyl alcohol as a carrier and applied to the mandril and pull wire such as by dipping.

The mandril is thereafter positioned within the IA tool by distal axial advancement through the proximal hypotube section and through the distal spring coil section. With the mandrel in place, a silicone or other suitable polymer is applied to the spring coil section of the IA tool 88 such as by dipping or painting as has been previously described. The silicone is cured as described, and the mandril is thereafter axially withdrawn from the IA tool.

Optionally, the end cap 112 is molded from a polymer such as silicone. This may be accomplished in a discrete step, or simultaneously with the coating operation. This is accomplished by extending the mandril axially slightly beyond the distal end of the spring coil and positioning a female mold cavity at the end of the coil having the desired interior shape. Preferably, the distal end of the mandril and/or the interior of the mold is provided with a pin to produce distal opening 90. All of the silicone components can be simultaneously formed, for example, by positioning the entire spring coil section of the device within a mold cavity and injecting the uncured silicone or silicone precursor.

This method produces a coil polymer composite IA tool having silicone or other suitable polymer segments 116 positioned between adjacent coil filars, as has been previously discussed. In addition, provision of the mandril during the polymer coating process in combination with the use of a polymer having a sufficiently low viscosity to flow through the adjacent coil filars, produces a tubular sleeve 118 on the radial interior surface of the spring coil 100 which has a substantially uniform interior cross-sectional area throughout. This eliminates, for example, the shelf 120 formed in this embodiment at the distal end of hypotube 94. In addition, interior tubular wall 118 encloses both the pull ribbon 108 and the deflection ribbon 102.

Isolating the interior lumen 92 from the pull ribbon 108 and deflection ribbon 102 is advantageous for several reasons. For example, in the IA embodiment, material is aspirated from inside of the eye. Interior sleeve 118 minimizes the possibility of that material getting hung up in the pull ribbon or deflection ribbon, to create a blockage within the central lumen. In non-IA embodiments, the interior sleeve 118 minimizes the likelihood that fiber optics or other medical implements passed through the sheath will damage or get tangled in the deflection ribbon or pull ribbon.

In addition, entrapping the pull wire 108 within a silicone sleeve 118 resists bowing of the pull ribbon 108 into the central lumen 92 when the pull ribbon is pushed distally in order to straighten the tip.

In an actual embodiment produced in accordance with the illustration contained at FIG. 7, the outside diameter of the coil was 0.040 inches. The coil was wound from a filar having a diameter of 0.0035 inches. A 0.006 inch gap was provided between adjacent filars in the deflection section. Each of the deflection ribbon and pull ribbon were made from 0.001 inch by 0.003 inch stock.

Figure 8:
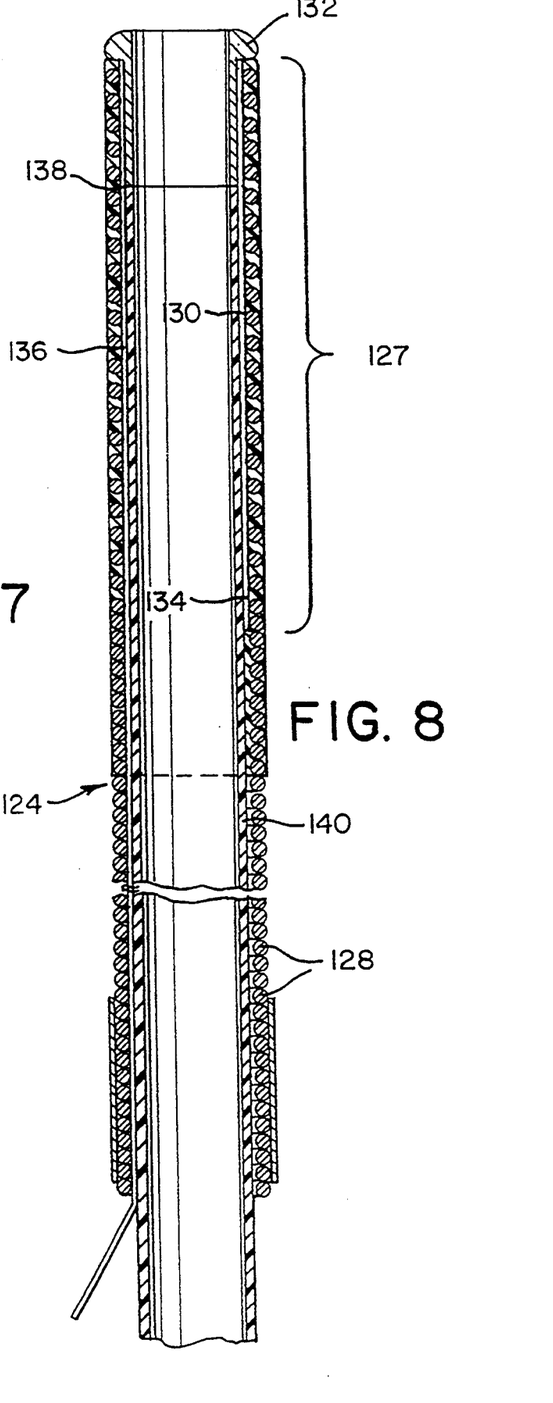
FIG. 8 is a cross-sectional elevational view of a steerable tubular sheath incorporating the coil polymer composite of the present invention.

Referring to FIG. 8, there is disclosed a steerable endoscope sheath incorporating the coil polymer composite of the present invention. Steerable sheath 124 generally comprises a coil body 126 having axially spaced adjacent filars in the distal steerable region 128 thereof. A deflection ribbon 130 extends from a distal point of attachment to end cap 132, to a proximal point of attachment 134. A pull ribbon 136 extends from a distal point of attachment to end cap 132, to a proximal control.

A silicone coating 138 is provided in manners previously discussed, to fill the spaces between adjacent filars 128 in the distal region of the flexible endoscope 124. In addition, the silicone coating 138 provides a smooth interior wall transition between the inside diameter at the distal end of the endoscope sheath and the interior diameter of an inner polyethylene tube 140.

In an actual embodiment of the design illustrated in FIG. 9, the outside diameter of the coil was 0.098 inches. The filar diameter was 0.010 inches, with a 0.006 inch gap between adjacent filars in the deflection section. The deflection ribbon had cross-sectional dimensions of 0.004 by 0.020 inches, and the pull ribbon had cross-sectional dimensions of 0.003 by 0.011 inches.

Although this invention has been described in terms of certain preferred embodiments, other embodiments that are apparent to those of ordinary skill in the art are also within the scope of this invention. Accordingly, the scope of the invention is intended to be defined only by reference to the appended claims.

We claim:

1. A steerable sheath, comprising:

an elongate flexible tubular housing, having proximal and distal ends and at least one central passageway extending axially therethrough;

a deflection element secured to the housing at a first point, and extending axially along the housing;

a pull element secured to the housing at a second point and extending axially along the housing, said second point rotationally displaced from said first point;

a spring coil in the wall of at least a portion of the housing; and an elastomeric coil interfit within at least a portion of said spring coil;

wherein axial proximal displacement of the pull element causes a lateral displacement of a portion of the tubular housing.

2. A steerable sheath as in claim 1, wherein said second point is rotationally displaced from said first point by at least about 90°.

3. A steerable sheath as in claim 2, wherein said second point is rotationally displaced from said first point by approximately 180°.

4. A steerable sheath as in claim 1, wherein said first point is within about 0.5 inches of the distal end of the sheath.

5. A steerable sheath as in claim 1, further comprising a force transmitter in a plane extending at a perpendicular to the longitudinal axis of the steerable sheath.

6. A steerable sheath as in claim 5, wherein said force transmitter comprises an annular ring.

7. A steerable sheath as in claim 1, wherein said elastomeric coil comprises silicone.

8. A steerable sheath of the type having an elongate flexible tubular body with a deflectable distal end and a high central lumen to outside diameter ratio, said sheath comprising:

a tubular housing;

a deflection element secured to the housing and extending axially along the housing;

a pull element extending axially through the housing and secured with respect to the distal end of the housing;

a spring coil in the wall of at least a portion of the housing; and an elastomeric layer extending along and in between adjacent filars of said spring coil;

wherein axial displacement of the pull element laterally displaces the distal tip of the housing and wherein the diameter of the central lumen extending through the housing is at least about 65% of the outer diameter of the housing.

9. A steerable sheath as in claim 8, wherein the diameter of the central lumen extending through the housing is at least about 75% of the outer diameter of the housing.

10. A steerable sheath as in claim 8, further comprising a lateral force transmitter at the distal end of the housing, for mechanically linking the distal end of the pull element to the distal end of the deflection element.

11. A steerable sheath as in claim 8, further comprising a proximal solid walled portion of said housing.

12. A steerable sheath as in claim 8, wherein said polymer comprises silicone.

13. A steerable sheath as in claim 12, wherein the silicone surrounds all sides of the spring coil along at least a portion of the length of the spring coil.

14. A steerable sheath as in claim 8, further comprising an outer tubular sleeve spaced apart from the housing.

15. An irrigation and aspiration tool comprising:
a tubular spring coil body, having a flexible distal region;
an elastomeric coil interfit within at least a portion of the spring coil body; and
a pull wire extending proximally from a distal end of the tubular body;
wherein proximal axial displacement of the pull wire causes a lateral deflection of the flexible end of the tubular body.

16. An irrigation and aspiration tool as in claim 15, further comprising a tubular sleeve radially outwardly spaced apart from the spring coil to provide an annular flow passage.

17. An irrigation and aspiration tool as in claim 16, wherein the tubular spring coil body is axially movably positioned within the tubular sleeve.

* * * * *